United States Patent
Guthrie et al.

(10) Patent No.: US 10,796,797 B2
(45) Date of Patent: Oct. 6, 2020

(54) SENSOR NETWORK FOR BREAST PUMPING MOTHERS

(71) Applicant: Moxxly LLC, Wilmington, DE (US)

(72) Inventors: Gabrielle V. Guthrie, San Francisco, CA (US); Santhi Analytis, San Francisco, CA (US); Cara C. Delzer, San Francisco, CA (US); Sam Cuttriss, Oakland, CA (US); Wisit Jirattigalachote, Palo Alto, CA (US); Paul Alan Wetter, Miami, FL (US)

(73) Assignee: Moxxly, LLC, Wilmington, DE (US)

( * ) Notice: Subject to any disclaimer, the term of this patent is extended or adjusted under 35 U.S.C. 154(b) by 41 days.

(21) Appl. No.: 15/011,549

(22) Filed: Jan. 30, 2016

(65) Prior Publication Data
US 2016/0220743 A1      Aug. 4, 2016

Related U.S. Application Data

(60) Provisional application No. 62/109,779, filed on Jan. 30, 2015.

(51) Int. Cl.
*A61M 1/06*       (2006.01)
*G16H 40/63*      (2018.01)
(Continued)

(52) U.S. Cl.
CPC ............ *G16H 40/63* (2018.01); *A61M 1/062* (2014.02); *G06F 3/0482* (2013.01);
(Continued)

(58) Field of Classification Search
CPC ........ A61M 1/062; A61M 1/064; A61M 1/06; A61M 1/0025; A61M 1/0031;
(Continued)

(56) References Cited

U.S. PATENT DOCUMENTS 4,314,484 A  *  2/1982  Bowman ............. A61M 5/1689
                                                73/861.41
6,440,100 B1    8/2002  Prentiss
(Continued)

FOREIGN PATENT DOCUMENTS

WO     WO 2013093739 A1 *  6/2013  ......... A61B 10/0045

OTHER PUBLICATIONS

Jacqueline C. Kent et al., Importance of Vacuum in Breast Milk Expression; Breastfeeding Medicine, vol. 3, No. 1, Mar. 2008, pp. 11-19; New Rochelle, New York, USA.
(Continued)

*Primary Examiner* — Kevin C Sirmons
*Assistant Examiner* — Tezita Z Watts
(74) *Attorney, Agent, or Firm* — Travis R. Banta; TechLaw Ventures, PLLC

(57) ABSTRACT

Disclosed herein is a breast pump sensor network. The breast pump sensor network includes an emitter disposed within a bodily fluid capture system and a detector disposed within the bodily fluid capture system. Further disclosed is a method for controlling the breast pump sensor network which includes emitting a beam of electromagnetic radiation within a bodily fluid capture system, detecting one or more drops of body fluid within the bodily fluid capture system, determining a bodily fluid flow rate based at least on the detected one or more drops of bodily fluid, and providing the determined bodily fluid flow rate to at least one user.

10 Claims, 12 Drawing Sheets

(51) Int. Cl.
*G16H 50/30* (2018.01)
*G06F 3/0481* (2013.01)
*G06F 3/0482* (2013.01)
*G06F 3/0484* (2013.01)

(52) U.S. Cl.
CPC ...... *G06F 3/04817* (2013.01); *G06F 3/04847* (2013.01); *G16H 50/30* (2018.01); *A61M 2205/13* (2013.01); *A61M 2205/3306* (2013.01); *A61M 2205/3334* (2013.01); *A61M 2205/3368* (2013.01); *A61M 2205/3379* (2013.01); *A61M 2205/3561* (2013.01); *A61M 2205/3584* (2013.01); *A61M 2205/3592* (2013.01); *A61M 2205/50* (2013.01); *A61M 2205/502* (2013.01); *A61M 2205/52* (2013.01)

(58) Field of Classification Search
CPC ........ A61M 1/0066; A61M 2205/3306; A61M 2205/3379; A61M 2205/3317; A61M 2205/50; A61M 2205/52; A61M 5/1411; A61M 5/1689
See application file for complete search history.

(56) References Cited

U.S. PATENT DOCUMENTS

| | | | | |
|---|---|---|---|---|
| 6,500,143 | B2* | 12/2002 | Suh | A61M 1/0066 119/14.01 |
| 2003/0204164 | A1* | 10/2003 | Britto | A61M 1/064 604/74 |
| 2005/0222536 | A1* | 10/2005 | Silver | A61M 1/064 604/74 |
| 2009/0318858 | A1* | 12/2009 | Dewey | G01F 1/7086 604/67 |
| 2010/0217148 | A1* | 8/2010 | Binder | A61B 5/4312 600/547 |
| 2014/0288466 | A1 | 9/2014 | Alvarez et al. | |
| 2016/0296681 | A1* | 10/2016 | Gaskin | A61M 1/06 |
| 2018/0050138 | A1* | 2/2018 | Alvarez | A61M 1/062 |

OTHER PUBLICATIONS

Donna T. Ramsay et al., Milk Flow Rates Can Be Used to Identify and Investigate Milk Ejection in Women Expressing Breast Milk Using an Electric Breast Pump; Breastfeeding Medicine, vol. 1, No. 1, Mar. 2006, pp. 14-23, New Rochelle, New York, USA.

* cited by examiner

SENSOR NETWORK FOR BREAST PUMPING MOTHERS

PRIORITY CLAIM

This application claims priority to U.S. Provisional Application No. 62/109,779, filed on Jan. 30, 2015, which is herein incorporated by reference in its entirety.

FEDERALLY-SPONSORED RESEARCH AND DEVELOPMENT

This invention was made without Government support. The Government has no rights in this invention.

FIELD OF THE INVENTION

This invention relates to a sensor network for breast pumps for nursing mothers.

Overview

Breastfeeding women rely on a breast pump to express milk while away from their babies, yet current breast pumps are not well suited to today's user. Designed decades ago, conventional breast pumps feature obtrusive parts that require access to a private space to undress; considerable time and effort to assemble and clean many parts; and a disjointed storage system that often results in milk spills. We have developed a smart breast pump system to allow women to pump anywhere and get real-time information about their milk supply. This disclosure teaches certain improvements that unlike existing flanges and bottles for pumping, is discrete and may be worn completely under regular clothing, without the need to disrobe or cover up with a blanket. The parts are simple to assemble and easy to wear. We augment the breast pump accessory parts (including flanges, bottles and tubing) with sensors and an accompanying software application that runs on the user's smartphone or mobile device. The sensors relay data such as volume pumped, flow rate and temperature data in real-time. The application also provides a network for mothers to communicate with each other and with experts in the lactation, prenatal, pediatric and post-partum care fields. The application connects with third party applications for extended tasks including to set reminders, see content and order supplies.

SUMMARY

Various aspects of the present disclosure are directed toward sensors that provide health information to a user. The system includes sensors that come in contact with human skin and/or bodily fluids, or are separated from skin and fluid by an apparatus. The apparatus provides a communication pathway that conveys information, from the object being sensed to the sensor. The pathway may be heat and light permeable. Sensor data is sent wirelessly to a smartphone application (app).

More specific aspects of the present disclosure are directed to the context of medical applications that record and monitor health information to alert users of health conditions and provide access to medical advice.

The application and sensors establish a smart, dynamic connection between the pump collection system and the user's ability to understand, by visualization and tracking the data collected during pumping sessions through a smartphone interface. The software content includes push notifications, APIs for interfacing to other baby apps and health tracking apps, and/or connections with other native apps (e.g. Photostream, Calendar, Music). The app is designed to answer users' questions regarding their milk supply, and track trends in terms of volume, optimal pumping times and inventory. Sensor data may also be used to monitor the general state of the user's health and alert them of potential complications, such as mastitis, when a fever or rise in body temperature is detected.

Accessories currently in the market do not sync with smartphone apps nor include sensors for milk supply monitoring and tracking. Herein, we disclose smart features including sensors that may alert a user of the real-time flow rate of milk expression, and may control a pump autonomously to regulate milk expression. The capture (flange) and collection (bottle) system fits under the user's clothes and is put on through the neck hole or from the bottom of the user's shirt, and is held to the body by any standard bra. The sensors between the capture and collection system measure flow rate and track aggregate volume pumped. Sensors within the capture system measure body temperature, and sensors within the connection and/or collection system measure milk temperature.

The breast pump sensor network includes an emitter disposed within a bodily fluid capture system and a detector disposed within the bodily fluid capture system. Further disclosed is a method for controlling the breast pump sensor network which includes emitting a beam of electromagnetic radiation within a bodily fluid capture system, detecting one or more drops of body fluid within the bodily fluid capture system, determining a bodily fluid flow rate based at least on the detected one or more drops of bodily fluid, and providing the determined bodily fluid flow rate to at least one user.

The above discussion/summary is not intended to describe each embodiment or every implementation of the present disclosure. The figures and detailed description that follow also exemplify various embodiments.

FIGURES

Various example embodiments may be more completely understood in consideration of the following detailed description in connection with the accompanying drawings.

Figure 10:
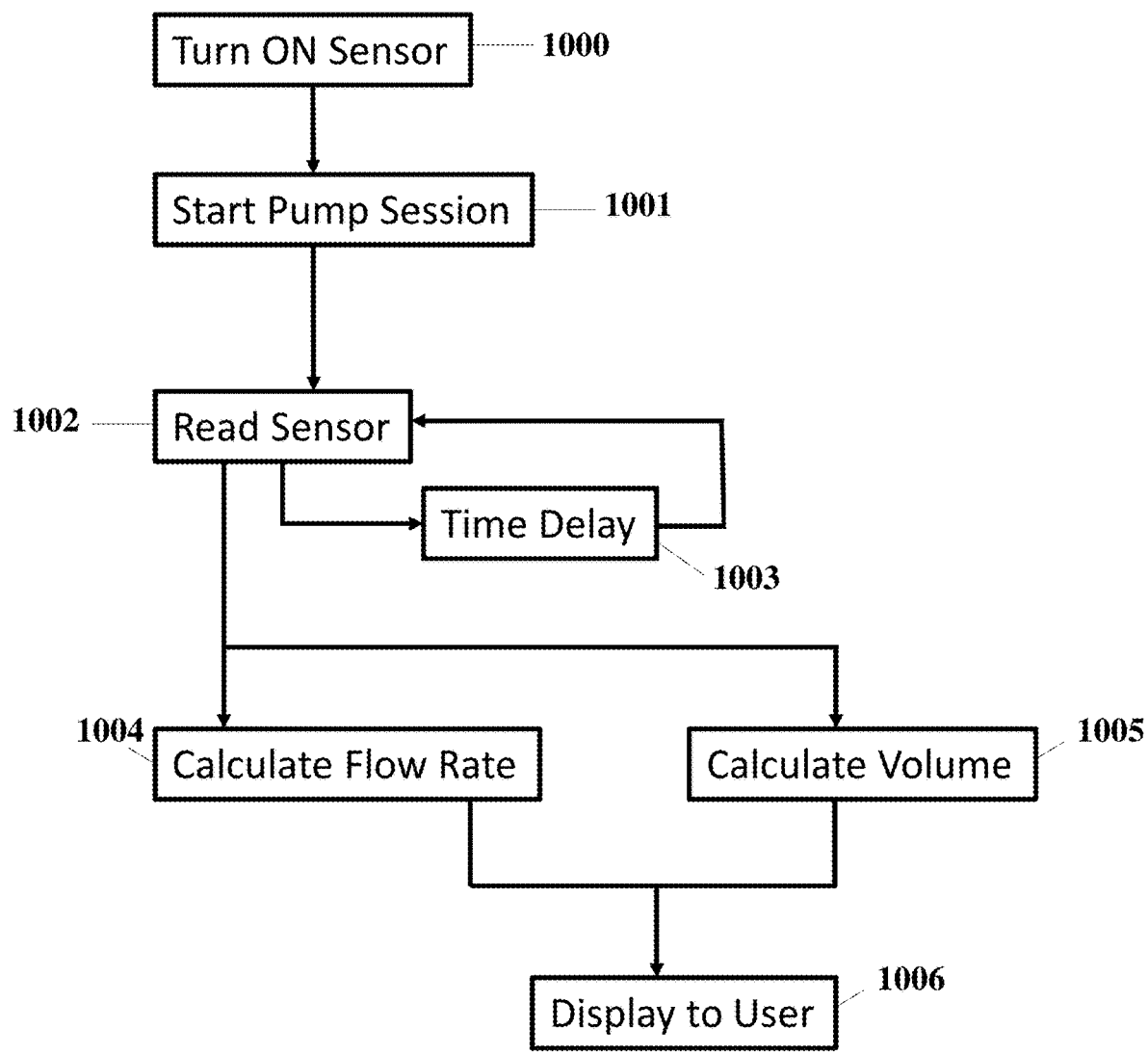
Figure 11:
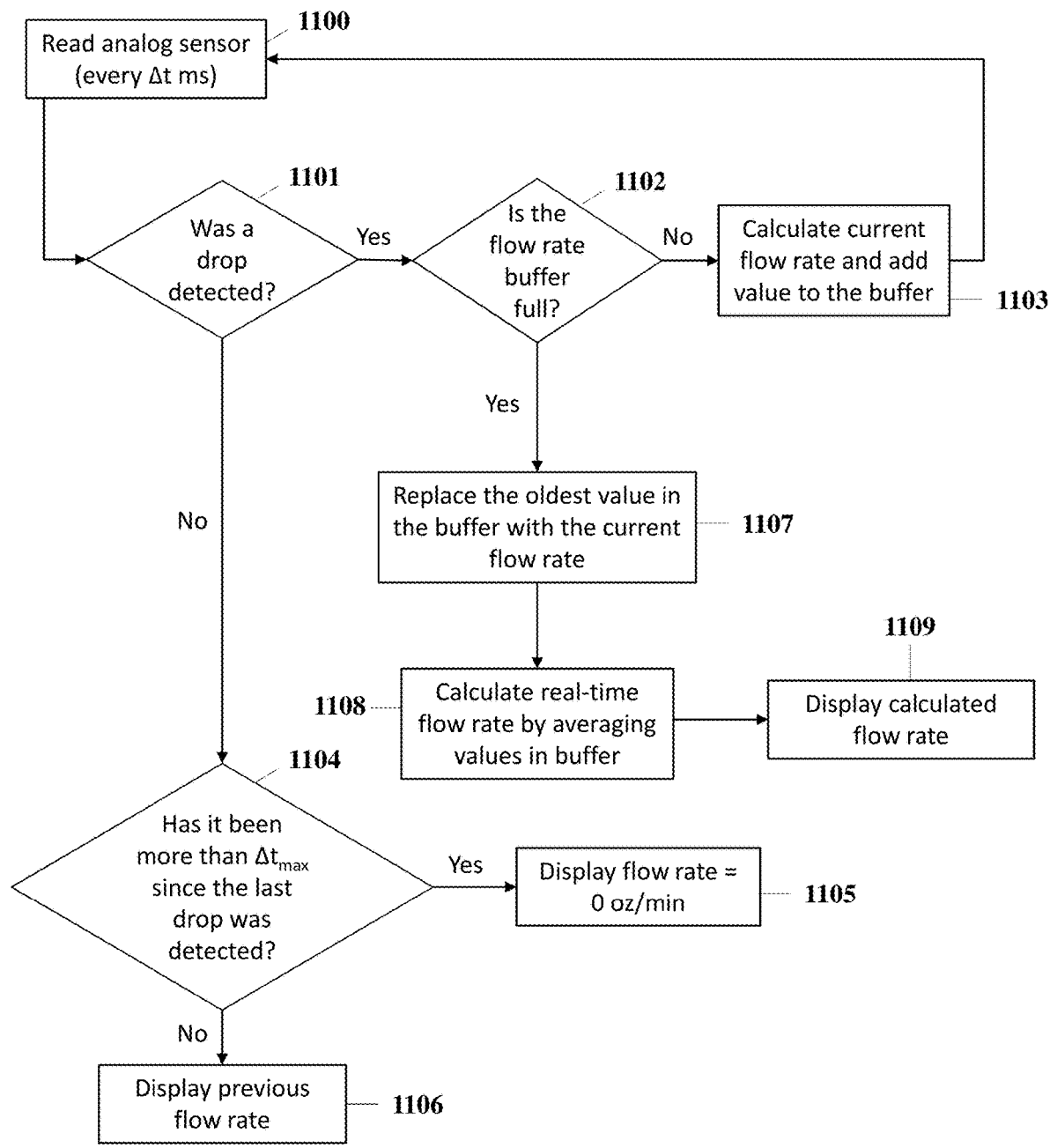
Figure 12A:
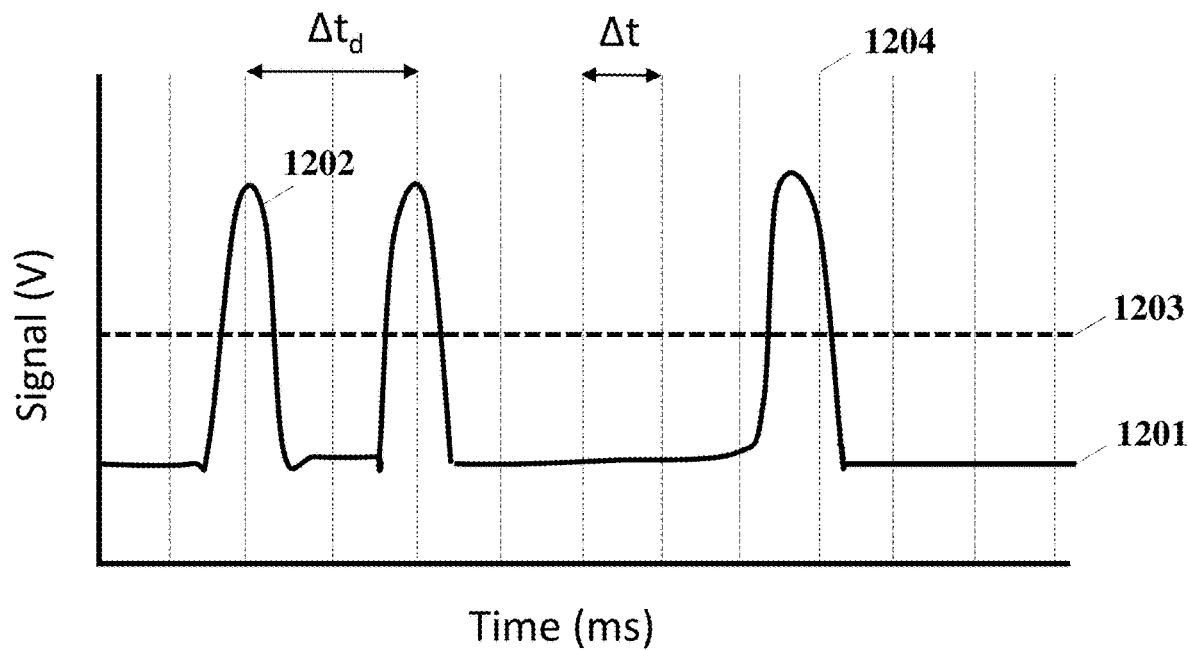
Figure 12B:
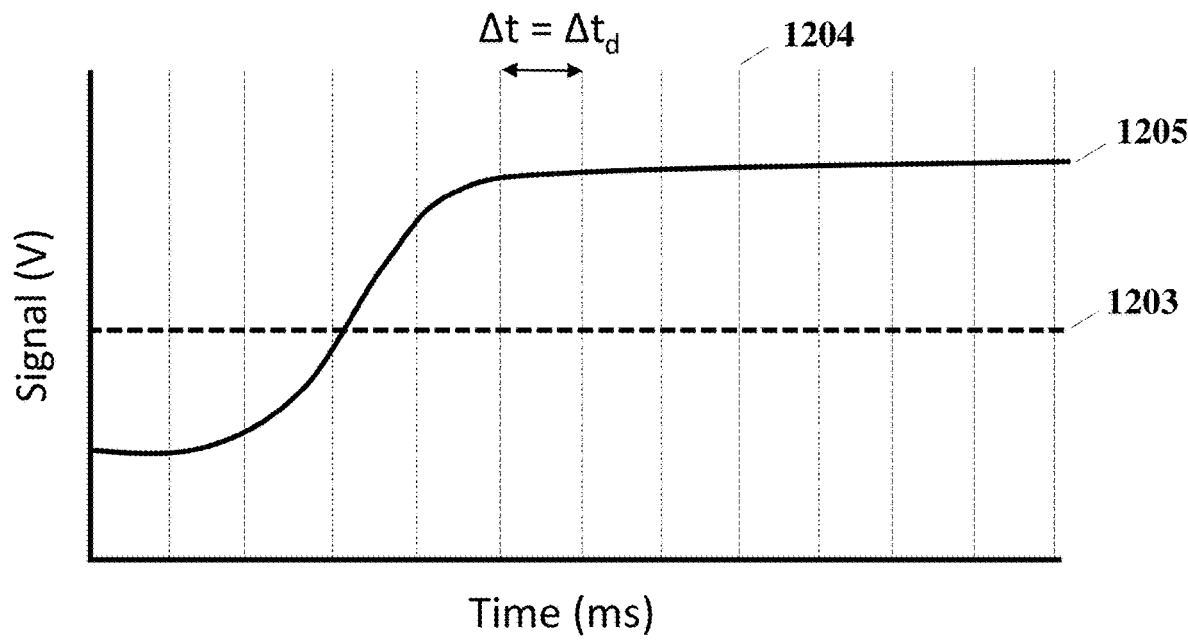

FIG. 10 demonstrates an example method of information flow for the sensor system;

FIG. 11 demonstrates an example method of data processing after the flow rate sensors are read;

FIG. 12A shows an example data set of sensor readings for when milk is dropping past the sensors; and FIG. 12B shows an example data set of sensor readings for when milk is streaming past the sensors.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims.

DESCRIPTION OF EXAMPLE EMBODIMENTS

Various aspects of the present disclosure are directed towards sensors and software to benefit breastfeeding and breast pumping users. Users include mothers and other caretakers including fathers, nannies, other family members, friends and medical personnel. Wearable sensors may measure data such as flow rate, volume, and temperature of milk expressed by means of a breast pump. While not necessarily so limited, aspects of the present disclosure are discussed in the example context of apparatus (e.g., devices, tools and systems) and methods involving a set of sensors to monitor the collection of bodily fluids.

Various aspects of the present disclosure are also directed toward methods that include a sensor network apparatus (e.g., devices, tools and systems) and methods involving a set of sensors to monitor the user's state of health. Skin temperature sensing to infer the user's body temperature may be employed by a thermal sensor either through direct or indirect contact with the body surface or with the breast milk.

Sensor data may be viewed by means of a software application that is executed on and accessed through one or more processors associated with any smartphone or mobile device application or through a web browser on a personal computer. Exemplary mobile devices that may execute or provide access to the software application include a smart phone, a tablet, a laptop computer, a desktop computer, a music storage and playback device, a personal digital assistant, or any other device capable of implementing a software application. These exemplary devices may include a combination of one or more application programs and one or more hardware components. For example, application programs may include software modules, sequences of instructions, routines, data structures, display interfaces, and other types of structures that execute operation. Further, hardware components implementing modules and other means disclosed herein may include a combination of processors, microcontrollers, busses, volatile and non-volatile memory devices, one or more non-transitory computer readable memory and/or storage devices and media, data processors, control devices, transmitters, receivers, antennas, transceivers, input devices, output devices, network interface devices, and other types of components that are apparent to those skilled in the art. While examples herein use a smart phone as an exemplary mobile device for controlling, interacting with, and receiving information from sensors, which will be discussed below, any device capable of executing an application program may be similarly used in place of a smart phone. Personal data may be encrypted and only available to a user by a password-protected interface. Users may access their data from on multiple devices; and multiple users may view a single user's data.

Temperature monitoring of the user's body temperature may take place each time she uses the breast pump accessory system. Two consecutive high temperature measurements will alert the user of an onset of fever. Such detection may help in the prevention of advanced stages of infection including mastitis or other complications with the mammary ducts.

Temperature monitoring of milk, whether breast milk, formula or other milk stored in the collection system may be conveyed by a processor to the inventory management system. The user may be alerted if the milk contained in a milk storage system is approaching a temperature range for an extended period of time that is not recommended for safe consumption. The alert may tell the user to refrigerate the milk or the storage system may automatically refrigerate the milk to keep the milk in a safe temperature range for storage before consumption.

The sensor triggers the processor to alert the user that the sensors are powered up and actively taking measurements. The sensor and processor may also indicate to the user if the sensor is OFF or not taking measurements by way of a user interface associated with the user's mobile device. Alternatively, the sensor may include an indication display such as an LED to alert the user of its status. The processor may convey the sensor status by means of text or a visual representation not limited to a glowing object. The glowing object may be represented as a light, a bottle or a bottle cover.

Information stored within one or more memory devices may be provided to a user to use in concert with lactation consultants, for example, through a referral service, through a method to call an expert directly from the user's phone, initiated from the mobile device, through posting to a forum answered by experts, or through text messaging. The user may pay additional fees for one on one consultations, and may get services for certain sessions for free or at a discount as a result of product promotions.

The mobile device may allow for the ordering of supplies, such as vitamins and supplements based on milk production trends or personal advice from medical experts via interaction with the user interface displayed on the mobile device. Other exemplary supplies include replacement parts for breast pumping systems, diapers and other food sources.

The mobile device may help the user control her milk supply inventory. For example, the processor may provide personalized notifications and/or messages, based on received sensor data, to the user of the time of day, week, etc. and suggested volume she should pump for specific regimes. An example regime may be to prepare for travel while away from the baby. In this example, the mobile device may provide advice to help the user increase milk inventory. Another example regime may include advice for weaning a baby off breastfeeding, and to lower milk production within a certain period of time.

The mobile device may give advice to mothers based on their babies' age and weight. For example, one suggestion the mobile device may provide is how much milk the baby should consume or should be consuming. This may give the user an indication for a quantity of milk she should breastfeed, pump, and supplement with formula to meet suggested full daily consumption amounts for a particular baby. The sensors may be utilized to collect data regarding milk trends for the processor within the device to match user profiles with baby age and other user characteristics to deliver relevant content to the user. User profiles may be identified by specific user personalities and proclivities. For example, one user profile may be referred to as the "earth mama" who pumps into glass bottles. Another example of another user profile may be referred to as "the juggler" who has to pump between work meetings. A mother that has certain pumping and milk storage trends may be identified by the sensor algorithm and content database.

The mobile device may help mothers keep track of milk volume that their babies are consuming even while breastfeeding, by estimating time of day pumped and duration of breastfeeding session. A sensor on the user's breast may be used to detect let down and measure milk flow. Sensors on the feeding bottle may also measure milk consumption.

In addition, the system may include the additional features. In one embodiment, the milk collection system may be leak proof. In order to reduce the size of the breast pump, a smart sensing component may be less than one square inch in height and width. The capture system may include a breast pump "flange" portion. The breast pump flange has a funnel like interior, and a bra cup shaped exterior portion. A rigid plastic section connects between a soft interior of the flange and the tubing to the pump. Rigid plastic snaps allow a collection system to connect to the capture system and to external accessories such as feeding nipples. The connection between the capture and collection system may be leak proof. The collection system may be cleaned and sanitized by dishwasher, microwave, hand-washing, or boiling.

The pieces of the catch and collection system may connect with minimal effort. They may utilize snaps, quick connects or twist methods of attachment. The sensors may turn ON when snapped in place, due to a mechanical switch, button, or magnetic connection. A visual cue in the form of a light may alert the user that the system is ON and ready to measure data. The data may be viewed in real-time on a display of the mobile device.

The sensors may be electrically connected to a microprocessor unit. The microprocessor unit may be electrically connected or part of an integrated circuit with a radio frequency (RF) communication unit such as Bluetooth. The RF unit may communicate to a smartphone application. The mobile device may send data wirelessly, such as over WiFi to a database server. Other suitable wired and wireless connections between the mobile device may be used to communicate information to a database server. Examples of these connections include ZigBee, Z-Wave, RF4CE, Ethernet, telephone line, cellular channels, or others that operate in accordance with protocols defined in IEEE (Institute of Electrical and Electronics Engineers) 802.11, 801.11a, 801.11b, 801.11e, 802.11g, 802.11h, 802.11i, 802.11n, 802.16, 802.16d, 802.16e, or 802.16m using any network type including a wide-area network ("WAN"), a local-area network ("LAN"), a 2G network, a 3G network, a 4G network, a Worldwide Interoperability for Microwave Access (WiMAX) network, a Long Term Evolution (LTE) network, Code-Division Multiple Access (CDMA) network, Wideband CDMA (WCDMA) network, any type of satellite or cellular network, or any other appropriate protocol to facilitate communication between the mobile device and the catch and collection system and/or a database server.

The mobile device may also be used to directly wirelessly control a pump motor. The user may turn ON or OFF the pump motor through the application interface, without having to touch the motor itself. Furthermore, the sensors may be used to determine when the processor may automatically turn ON or OFF the pump motor, without direct user intervention, based on whether a time based goal or volume based goal has been reached. In addition, the sensor data may be used by the processor to turn ON or OFF the pump motor or increase or decrease pump suction and oscillation pattern dependent on flow rate of milk expressed.

The sensor and smartphone system may automatically track data specific to the left and right breasts. The sensors may utilize piezo elements, switches, accelerometers, or tilt or knock sensors to identify to the processor the left and right breasts. The mobile device may read the received signal strength from one or both microprocessors in each pump unit and store data for the left and right breasts in a memory device. Alternatively, one microprocessors may be a peripheral to the other unit, such that the right sensor always communicates in near range via a specific radio frequency to the left sensor, which then communicates over Bluetooth to the smartphone. Alternatively, the smartphone application may be able to determine which unit is worn on the left or right breast by reading a codified element such as a serial number, stored in the firmware of the sensor's microprocessor. In addition, the sensors may have a visual indication on the chassis of the sensor components to notify the user which side is to be worn on the right or left data for consistent data collection. Alternatively, the smartphone application may be able to determine which unit is worn on the left or right breast by directing the user to move the smartphone over a specific unit and reading its received signal strength, such as measured by an RSSI value.

Smart system components may include sensors to measure and track flow rate of milk expression. The smart system components may include sensors to measure volume of milk pumped. The smart system components may include sensors to indicate proper positioning of the catch and collect system for milk extraction. The smart system components may indicate when all parts of the system are connected and ready to start collecting data. Data from the sensors may be transmitted to the mobile device. The smart system components may be charged inductively when a sensing element is placed inside a carrying container or charging dock. The smart system components may be charged through a proprietary contact charger when the sensing element is placed inside the carrying container, and/or may be charged through an electrical connection such as USB. It is to be noted that while USB is an acceptable electrical connection, there exist a myriad number and types of connectors in the art, many of which may also be suitable as electrical connectors. The carrying container may be in the form of a box, bag, purse, or clutch. The carrying container or charging dock may be powered by, for example, a micro USB to a standard USB-A port. The carrying container or charging dock may be powered via a proprietary contact charger to a standard USB-A port. Alternatively, the sensing elements may each have a micro USB port to connect to a micro USB to USB-A cable. The cable may have multiple divisions to simultaneously connect to multiple sensors for charging a battery and/or data transmission. Data from the sensors may also be stored on-board and later sent wirelessly to a receiving system. The sensor device may be water resistant. The sensor device may further turn OFF or enter a STANDBY mode to save power after the device has stayed still or not collected new data for a specified length of time.

The device may pair with the smartphone through an initial setup step. Anytime after the initial device to phone pairing, when the device is ON, data from the sensors may be stored on board in a microprocessor. Data from the microprocessor may be sent over BLE to a smartphone application. Once the data is received by the phone, it may be erased from the microprocessor. Onboard memory may be capable of storing data for multiple pumping sessions that average 10 to 30 minutes each. Data stored on microprocessor may include real-time flow rate in oz/min gathered at an interval that may range from every 1 to 30 seconds. Data may include total volume pumped per pumping session. The device may turn OFF to save power after no new information is gathered after a specified length of time.

The mobile device may communicate over BLE to the smart accessory (which may be in the form of a sensor module). The processor within the mobile device may encrypt and send data to the server. Data may be decrypted to view on a web-browser by the user tied to the data. Users may access their data for email backup and downloading. All user data may be saved. The data may be synchronized to new devices. New participants may also see previous data including trends and messages. The mobile device may include an Open API for third party app developers to include features for users of the smart accessories.

The embodiments and specific applications discussed herein may be implemented in connection with one or more of the above-described aspects, embodiments and implementations, as well as with those shown in the appended figures.

Figure 1A:
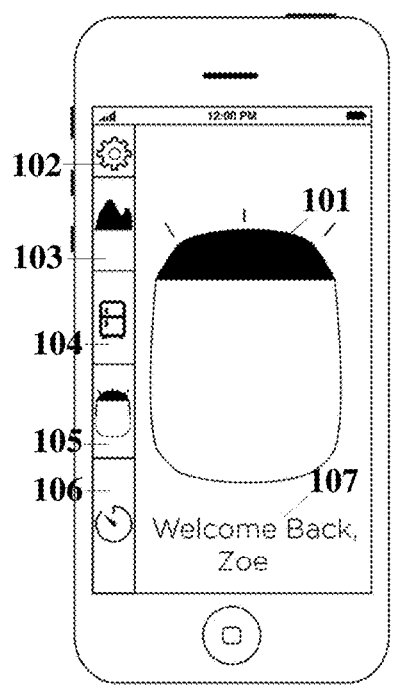
FIG. 1A shows an example graphical user interface display including a personalized greeting and access to a home menu to select how a user may start her pumping session.
Figure 1B:
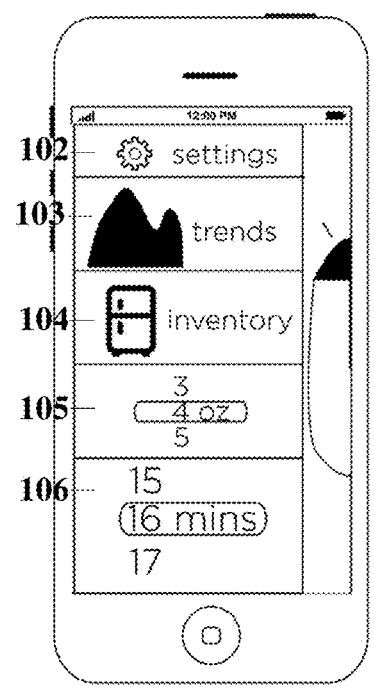
FIG. 1B shows an example graphical user interface display including a home menu to select how a user may start her pumping session.
Figure 1C:
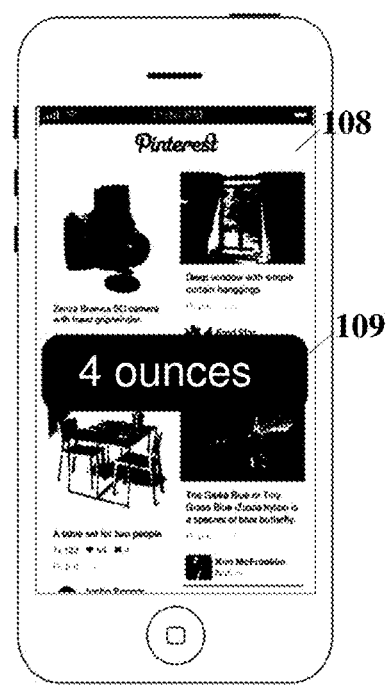
FIG. 1C shows an example push notification from the app, as viewed when the user is in another app.

Turning now to the figures, FIG. 1 shows example graphical user interfaces, consistent with various aspects of the present disclosure. FIG. 1A demonstrates an example home screen with a greeting 107 for the user. A glowing object 101 is shown as an indicator that the smart system has been started, or is powered ON, or is actively gathering data. In this embodiment, the glowing object is the top of a bottle of milk. A side menu shown in FIGS. 1A and 1B displays an interactive graphical user interface elements to access the settings 102, data trends 103, and milk supply inventory 104. The graphical user interface images portrayed may operate on a multi-touch screen. The user may choose to run a pump session using graphical user interface elements such as volume goal 105 or a time goal 106. For a volume goal 105, the user will be notified when she has pumped a total amount of milk equal to the goal amount. For a time goal, the user will be notified when she has pumped a total amount of time equal to the goal amount. Once a time goal is reached, the smart system may feedback information allowing the user to turn OFF the pump via the mobile device using one or more graphical user interface elements. Other graphical user interface elements may include diversions, such as games, or curated content including tips, articles, offers and discounts. Some graphical user interface elements may also allow for the user to order items and shop from the smartphone. Other graphical user interface elements may also allow for the user to keep track of personal information about her baby, such as age, weight and medical appointment schedules. This information may be used by the sensor system in addition to sensor data to alert the user of actions to take to follow a meal plan or visit a doctor. As shown in FIG. 1C, if the user is active in another native application 108, a push notification 109 or message may alert the user of their current total volume pumped. Push notifications may also convey duration of the session, flow rate, or temperature information. Push notifications may also be used to remind users of a time to pump. The sensors and/or mobile device may alert the users of a scheduled pump time through indicators such as lights, vibrations, noises, or push notifications. Push notifications may be text notifications sent to the user's native text messaging application or SMS service. Push notifications may be in the form of silent notifications that appear on the user's native notification panel or pop up as a new window. Push notifications may include text and/or emojis and/or animations. In one embodiment, push notifications may be pre-delivered and run in the background of the native operating system; thus when the user opens the breast pumping application, the notification is readily seen. Notifications may be sent via a third party software development kit (SDK), and may be encrypted or directly sent in a data payload. The data payload may be a JSON packet or other packet of information containing data and metadata. The data payload may also refer to data sent from the mobile device via the software application to a network server or, alternatively, the data payload may also refer to data sent from one or more sensors associated with the capture and/or collection systems to the mobile device.

Figure 2A:
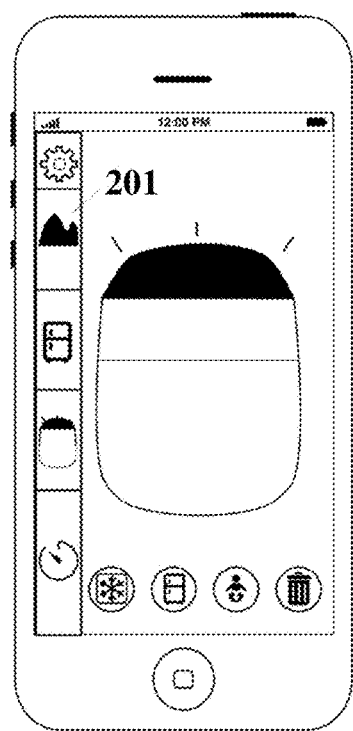
FIG. 2A shows an example graphical user interface display including a home menu to select what type of data the user would like to review.
Figure 2B:
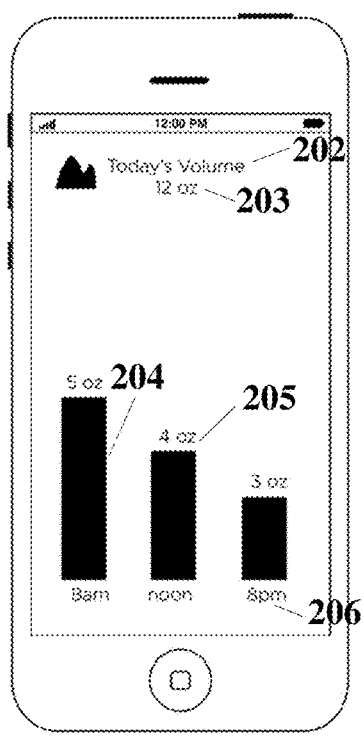
FIG. 2B shows an example graphical user interface display displaying trends in daily volume pumped.
Figure 2C:
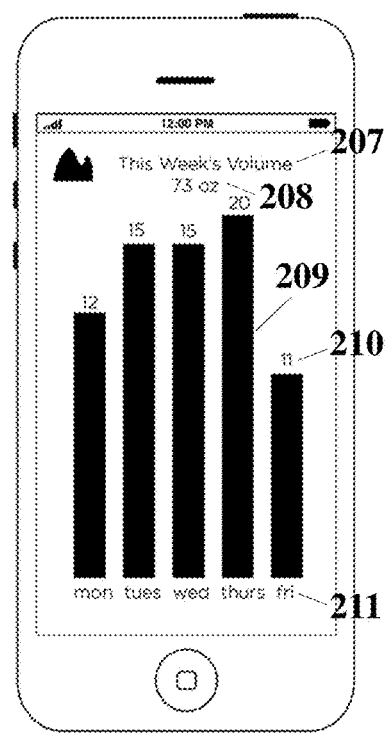
FIG. 2C shows an example graphical user interface display displaying trends in weekly volume pumped.

FIGS. 2A-2C show exemplary graphical user interface elements, consistent with various aspects of the present disclosure. FIG. 2A demonstrates an example display with a method to view trends in data from a tab 201 in a main menu. FIG. 2B demonstrates graphical user interface elements that provide information such as the daily volume pumped 202, the running total value 203, one or more bars representing different pumping sessions 204, including a total volume per session 205, and the time of each of the pumping sessions 206. FIG. 2C demonstrates a graphical representation of the weekly volume pumped 207, while displaying the week's running total value 208, with a bar representation for each day 209, including a total volume per day 210, and the day of the week 211. The user may touch one bar 209 in the weekly view to see more details in a daily view. The daily view may give more specific trend information of pump sessions pumped per day. Also, the user may pinch daily bar graphs in the weekly view to zoom in and out to, for example, view 4 days or 7 days of total volume data at a time.

Figure 3A:
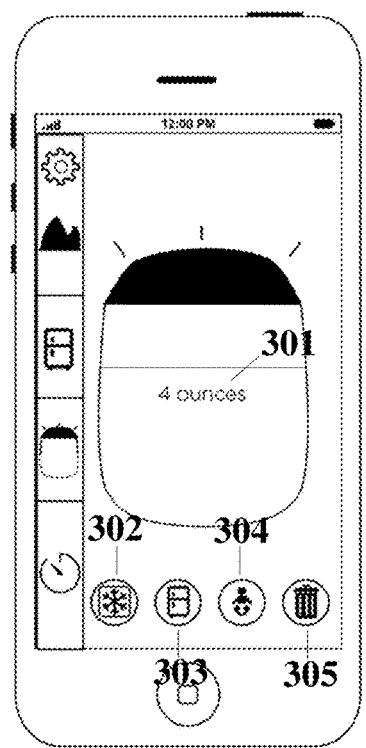
FIG. 3A shows an example graphical user interface display displaying volume pumped in real-time and categorize the milk for inventory.
Figure 3B:
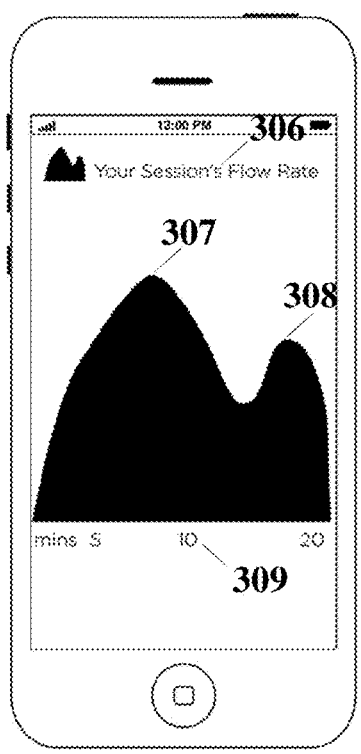
FIG. 3B shows an example graphical user interface display displaying trends in in-session flow rate.
Figure 3C:
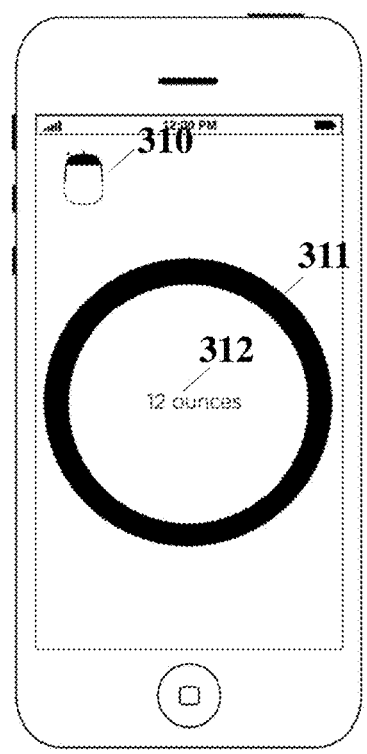
FIG. 3C shows an example graphical user interface display displaying volume pumped daily.

FIGS. 3A-3C show exemplary graphical user interface elements, consistent with various aspects of the present disclosure. FIG. 3A demonstrates graphical user interface elements that provide an indication of the real-time volume pumped as an animation of milk filling a bottle. An alternative display method shows the real-time volume pumped as an animation of liquid filling up the entire screen of the smartphone or mobile device. Alternatively, any object, including rings and circles may be used to indicate filling of volume. An object may be animated to pulse according to the real-time flow rate of the milk as measured by the sensors. The real-time volume may also be numerically displayed 301. At the end of the pumping session, the user has the ability to categorize and log the volume information in order to track milk inventory. The virtual bottle may be dragged into the freezer icon 302, or the refrigerator icon 303, or the baby icon 304, or the trash icon 305. The freezer milk may be automatically saved with information including date and time of pumping session and total volume pumped. The refrigerator milk may be automatically saved with information including date and time of pumping session and total volume pumped. Further categorization may be made for the location of the milk stored, for example at home, at work, at daycare, and etc. Milk fed directly to the baby may be automatically saved with information including date and time of feeding session and total volume pumped. The mobile device may allow for users to deduct milk from the inventory system when they use the stored milk. The sensor system may alert the user when milk in the freezer or fridge is about to expire. The sensor system may alert the user when milk in the fridge should be moved to the freezer to extend its shelf life based on time, storage temperature, and/or recommended guidelines. Users may choose to trash data 305, if for some reason the session should not be saved, including if the milk was rejected or not used. FIG. 3B demonstrates graphical user interface elements that display the flow rate throughout the pumping session 306 as a solid graph. The graph may be shown in real-time or post-session. The user may see her peak flow rate 307, and the moment of second let-down 308 with respect to the time 309 from the start of the session. The application will help users learn how they may be able to pump more efficiently by being aware of whether or not they may pump more milk in a specified period of time due to multiple let-downs. The user may also choose to stop pumping when she has been made aware of a continued lag in flow rate. The user may also be encouraged to keep pumping when their flow rate is high and more milk may be captured than if she ended their session too early. FIG. 3C shows a volume icon 310 associated with a display that shows the total volume per session or per day. A circular representation or pie chart 311 of total volume in relation to a goal volume 312, provides the user with information regarding how much breast milk is available and how much milk needs to be supplemented, for example with formula. The ring 311 may have sections of various colors to represent breast milk pumped, expected breast milk to be pumped, and other food sources to feed the child for a given day.

Figure 4A:
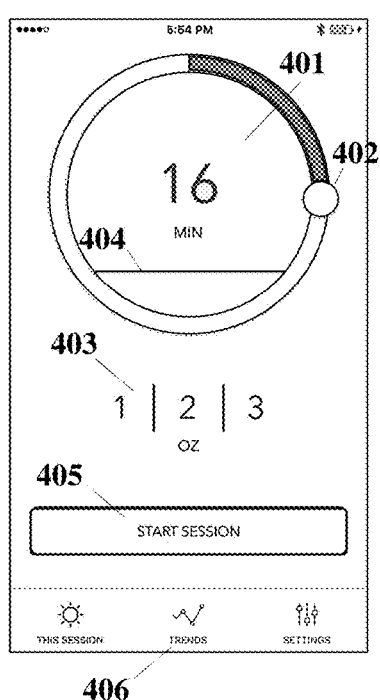
FIG. 4A shows an example graphical user interface display displaying an interface which allows a user to set a time and volume notification at the start of a pump session.
Figure 4B:
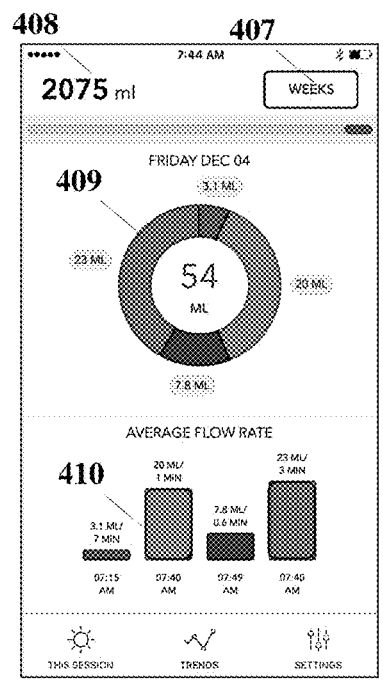
FIG. 4B shows an example graphical user interface display visualizing trends in volume pumped over multiple pump sessions.
Figure 4C:
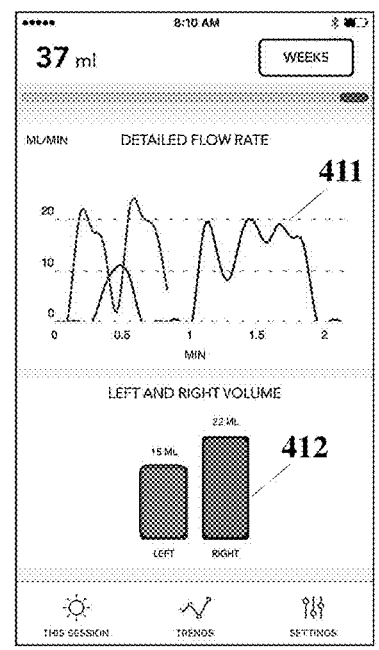
FIG. 4C shows an example graphical user interface display to visualize trends in milk flow rate and volume pumped by the right and left breasts.

FIGS. 4A-4C show exemplary graphical user interface elements, consistent with various aspects of the present disclosure. FIG. 4A illustrates an alternative method to set a time and volume notification at the beginning of a pump session. The user may set a timer 401 by dragging a ball 402 around a circle representing a 60 minute clock. The pump volume may be set by scrolling a volume menu 403 left or right to decrease or increase values. The volume unit of measurement may be changed in the settings to toggle between ounces or milliliters based on the user's preference. Alternatively, a fill line 404 inside the circle interface may be dragged up or down to set a volume goal for a session, in which a text indication such as 403 is automatically selected. Once one or more of the notifications are set, the user may touch the "Start Session" button 405 to start collecting data from the smart breast pump and sensor system. 405 may be selected after manually starting the pump motor. Alternatively, selecting 405 may cause a signal to be sent to the breast pump system to automatically turn ON the pump motor. During pumping, the user may choose to interact with the mobile device. For example, the user may choose to see the timer or swipe across the timer or other part of the user interface to see photos of her baby. It has been shown that seeing and hearing a baby helps with milk let down in nursing mothers. Anytime, the user may select "Trends" 406 to view data collected by the sensor system, not limited to volume pumped, flow rate of milk expressed, and body temperature. FIG. 4B demonstrates an example embodiment of a daily view of trends. A user may select a weekly view by selecting "Weeks" 407. An overall volume pumped value 408 may represent the total volume pumped in a lifetime, or month, or week, or day. A ring shaped pie chart may indicate the total volume pumped per session 409, organized by different colors. The color used in the display per session may be constant for all trend data for a particular day. A session total volume over pump session duration gives the user an idea of the average flow rate per session 410. More information may be provided when the user scrolls down on the daily view, as represented in FIG. 4C. FIG. 4C shows an exemplary embodiment of the flow rate throughout a session, represented by a line graph, where each line 411 represents a single pump session. Information such as total volume pumped per day per breast, may also be graphically represented 412.

Figure 5:
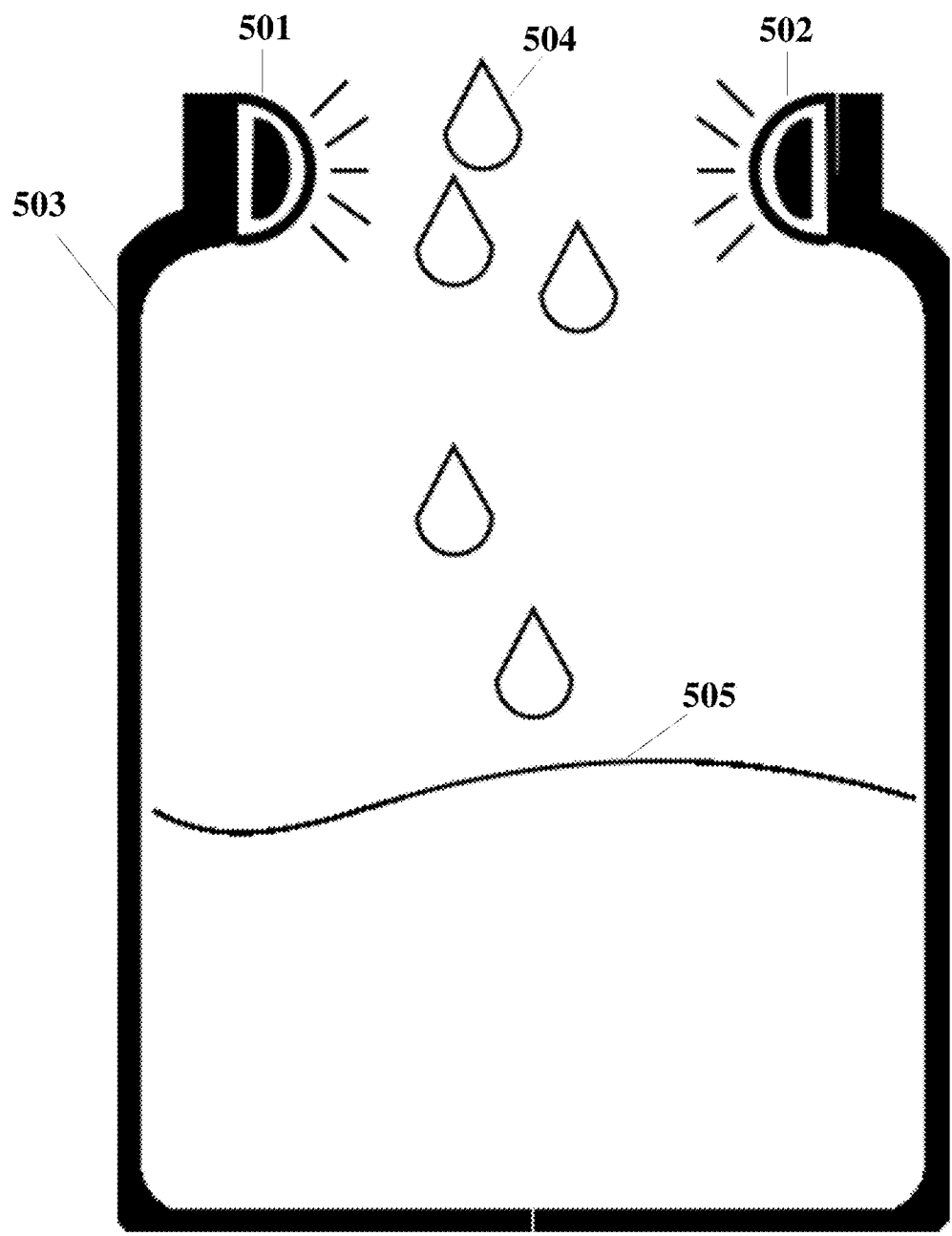
FIG. 5 shows an example location for one or more sensors on the collection system.

FIG. 5 shows an example location for one or more sensors on the collection system. Either one sensor 501 or more sensors 502 may be located at the neck of a bottle or collection container 503, in order to measure data as read from milk dropping 504 or streaming into the collection system and filling it with milk 505. The sensor 501 or 502 may be measuring flow rate or temperature or counting drops. The sensors may also measure other content from the milk including nutritional information such as fat or calorie content. Further, the sensors may indicate caffeine or alcohol content in the milk. Flow rate and volume sensors may include optical-based drop counters such as laser diodes or IR LEDs, or water wheel type apparatuses utilizing electromagnetic radiation sensing methods such as Hall effect sensors or coils or mechanical counting methods using switches or force sensing techniques. Flow rate and volume sensors may also be capacitive, by measuring changes in the proximal environment with and without the presence of milk. Flow rate and volume sensors may also be based on liquid level measurements by means of capacitive sensors, ultrasonic sensors, microphones or optical sensors based on light or sound reflectivity.

Figure 6A:
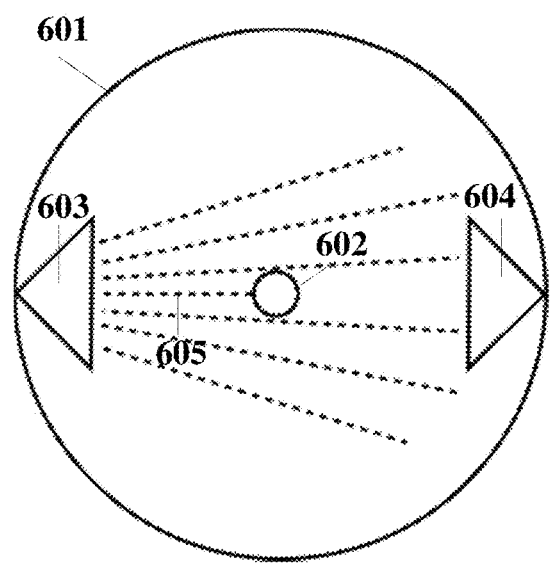
FIG. 6A shows an example configuration for the sensing elements.
Figure 6B:
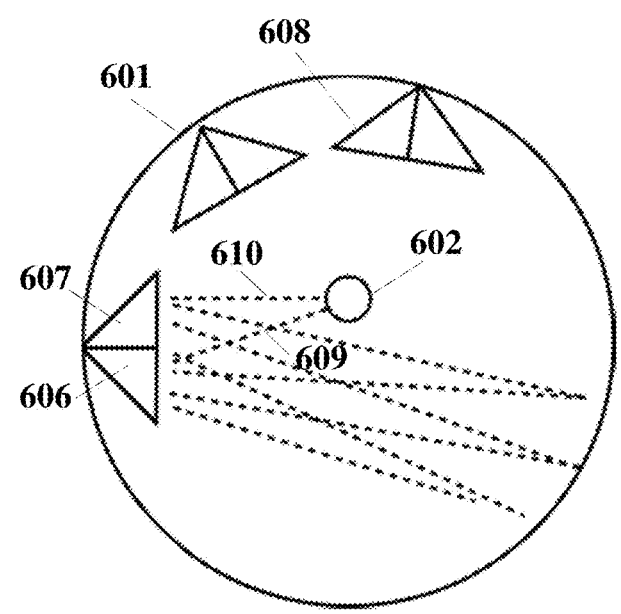
FIG. 6B shows an example configuration for the sensing elements.

FIGS. 6A-6B shows example configurations for the sensing elements. These elements may be placed in the path of the milk flow. The configurations are demonstrated in the top cross-sectional view of the area between the capture and collection system, or the area at the neck of the collection system. The configurations described optically detect the presence of milk either by measuring blocked light or by measuring an increase in reflected light. These configurations may also include a temperature measuring apparatus such as a thermopile, infrared (IR) temperature sensor, heat sensitive resistor or other temperature-measuring sensor. FIG. 6A shows a configuration where an emitter 603 and detector 604 are placed pointing at each other within the boundaries 601 of the system. In other words, emitter 603 and detector 604 may be disposed as facing each other on substantially opposite sides of a milk collection device. The emitter emits a light beam 605 towards the detector 604. In the presence of a drop or stream of milk 602, the light beam is blocked from reaching the detector 604. The sensor configuration thus measures a break in the light path by sampling light measurement data in accordance with a particular timing algorithm such that a processor associated with emitter 603 and detector 604 may determine whether a single drop or a stream of milk is passing by. Calculation of the volume passed may be done on the microprocessor electrically connected to the sensors, or done on the smartphone application in real-time. FIG. 6B shows an alternate configuration where each emitter 606 and detector 607 pairs 608 are placed side by side within the boundaries 601 of the system, such that they detect light reflecting off the opaque surface of the milk 602. A beam of electromagnetic radiation 609 from the emitter 606 hits the falling milk 602 and is reflected 610, and is detected by the detector 607. Alternatively, heat radiation (such as IR) emitted by the milk is measured passively by the sensor, for example, to detect heat of the object.

Figure 7A:
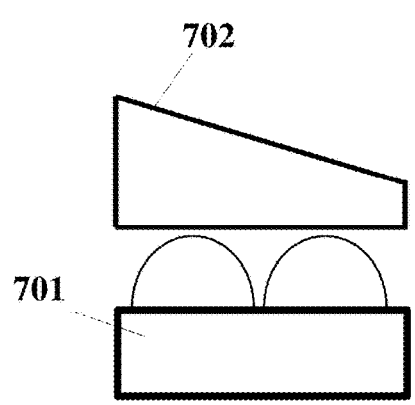
FIG. 7A shows an example lens configuration for the sensing elements.
Figure 7B:
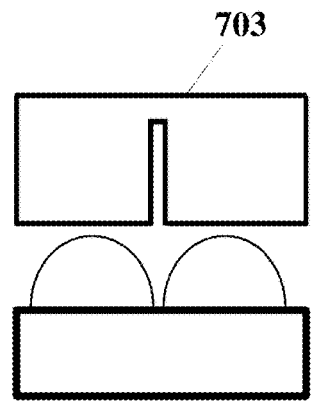
FIG. 7B shows an alternate example lens configuration for the sensing elements.
Figure 7C:
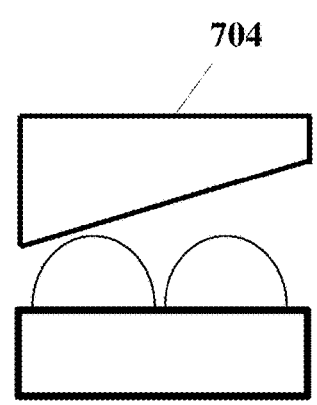
FIG. 7C shows an alternate example lens configuration for the sensing elements.

FIGS. 7A-7C show exemplary configurations of lenses that may be used for directing emitted and detected electromagnetic radiation. An emitter and detector pair 701 may be placed against a lens that is shaped in such a way to ensure electromagnetic radiation leaving the emitter does not enter the detector until it is reflected by an external object within a detection volume of interest. Lens 702 in FIG. 7A is configured to control the detectable volume to a specific location, primarily off-center to the emitter-detector pair. Lens 703 in FIG. 7B and lens 704 in FIG. 7C are example embodiments configured to control the internal reflections of the emitted electromagnetic radiation away from the detector, and to direct only external reflections into the detector. The various lens configurations may be reconfigurable to move the detectable volume of interest based on the way milk falls past the sensor. The lens may be permeable to the electromagnetic radiation emitted by the sensor. For example, for an IR emitter/detector pair, the lens is made using an IR transmitting material, with properties allowing for transmission at the emitter's wavelength. The IR transmitting material may appear opaque or translucent to the naked eye, and be made of glass or plastic, not limited to polycarbonate, polypropylene, ABS, polyester, acrylic, nylon or any composite material.

Figure 8:
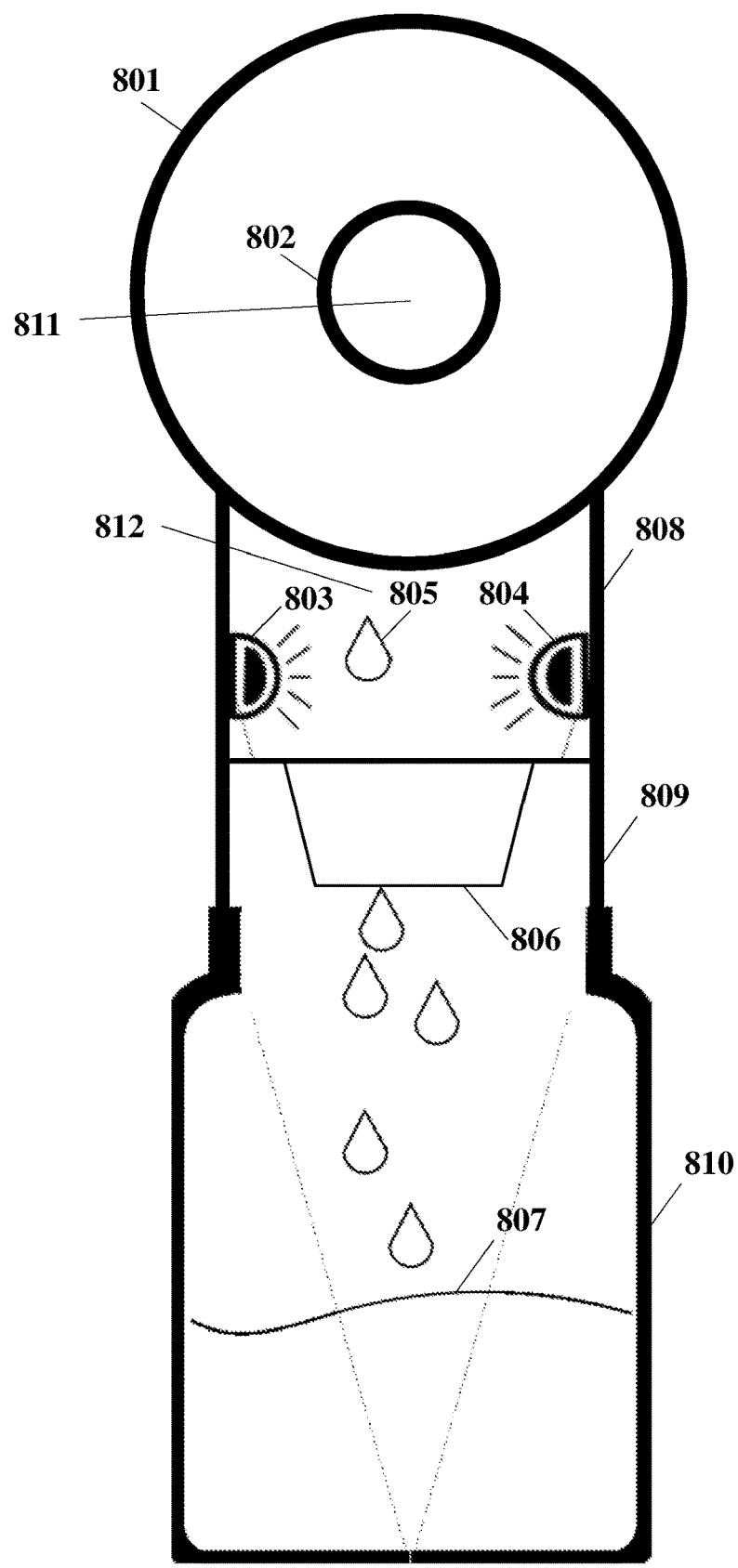
FIG. 8 shows an example location for one or more sensors between the capture and collection system.

FIG. 8 shows an example location for one or more sensors between the capture and collection systems of a breast pumping accessory for expressing milk. The capture portion, also known as the flange, is bounded by 801, which cups the breast and seals against it, with an extension 802 that surrounds the nipple. As milk 805 leaves the nipple and falls in the connection area 808 below the flange 801 and above the capture system 810, it is detected by one sensor 803 or multiple sensors 804. The location of 803 and/or 804 may be used for milk temperature sensing. In this example, the sensors are placed above a valve such as a duckbill 806, which is closed when suction is applied to the nipple and then opens under positive back pressure, allowing milk 807 to fill the bottle. The suction and back pressure is caused by oscillating motions within the system, either from an electric motor or a manual action. A spout region in the milk collection system disposed between 802 and the sensors in the milk capture system may be constrained by a spout 811 that directs the way milk falls past the sensor 803. The spout 811 may be an extension of the nipple region 802, and may allow for milk to pool in a reservoir 812 in the milk capture system and fall in a controlled manner in drops that are detected by sensors 803 and 804. The spout may break the surface tension of breast milk and use gravity to ensure the milk falls in drops of a specific known size and shape past the sensor, such that each drop contains a uniform volume of a bodily fluid, such as milk. A multiplier, representing volume per drop of milk, in a milk sensing algorithm may be set or altered based on the spout configuration.

Figure 9A:
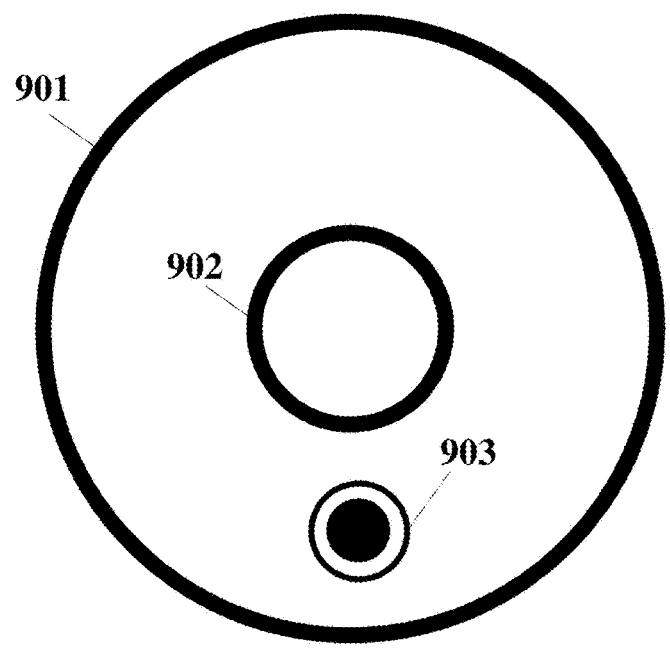
FIG. 9A shows an example location for one or more sensors on the capture system in a front cross-section view.
Figure 9B:
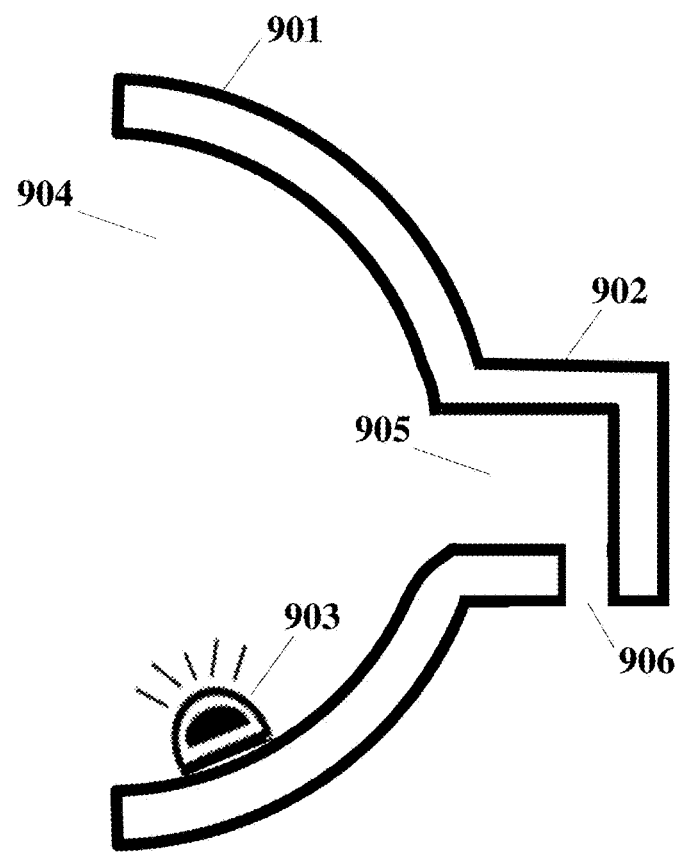
FIG. 9B shows an example location for one or more sensors on the capture system in a side cross-section view.

FIGS. 9A-9B shows an example location for one or more sensors on the capture system. FIG. 9A shows the sensor in a front cross-section view; and FIG. 9B shows the sensor in a side cross-section view. The sensor 903 is located on the flange 901 such that flange 901 makes direct or indirect contact with the user's breast including the skin surface, areola or nipple areas. The location of sensor 903 may be used for body temperature sensing. In FIG. 9C, the portion of the flange 901 that surrounds the nipple 902, has an outlet 906 for milk to pass into the collection system. The breast is cupped with the flange in the area 904, and the nipple is positioned in area 905.

FIG. 10 demonstrates an exemplary method of information flow for the sensor system. After the sensors are turned ON at step 1000 and a software application begins execution on a mobile device, the user starts a pump session at step 1001. The sensors are read at a specific sample rate at step 1002 as determined by a time delay 1003. The time delay may be a delay coded in the microprocessor firmware or in the software application, the clock speed, or interrupt timer of the microprocessor and may account for any delays or latencies in receiving, processing, and transmitting data between the hardware and software components. After the sensors are read in step 1002, an algorithm, shown in FIG. 11 which will be discussed below, calculates the current flow rate 1004 and total volume pumped 1005. The microprocessor provides this information to the user via a mobile device either by display in the software application or through a web browser-based interface 1006.

FIG. 11 demonstrates an exemplary method of data processing after the flow rate sensors are read. After a specified time period $\Delta t$, on the order of milliseconds, based on the micro-processor sample rate and time delays as previously explained, the analog sensor value is read by the microprocessor at step 1100. The specified time period $\Delta t$ or the number of samples are operated on by an averaging filter to increase the accuracy of flow rate detection at step 1101. If a drop is not detected at step 1101, the time since the last drop was detected is checked at step 1104. If, within a predetermined amount of time $\Delta t_{max}$, on the order of seconds, no new drops are detected, a data buffer is cleared and a flow rate of 0 is displayed at step 1105. Conversely, if a drop has been detected within the $\Delta t_{max}$ time period at step 1104, the microprocessor directs a display device to display the previously calculated flow rate at step 1106. Drop detection is performed by comparing the sensor's analog sensor reading, such as an ADC value, to the buffer's average within some preset threshold. The threshold may be programmed in the sensor's firmware and changeable, either by upgrades, based on calculations in the algorithm or periodic autonomous calibration. In one embodiment, the number of samples that are filtered is equal to the length of a data buffer. It is also to be noted that the data buffer may be implemented as more than one physical memory unit or software based implementation.

If a drop is detected at step 1101, a microprocessor determines whether or not the flow rate buffer is filled with data values at step 1102. If the buffer is not full at step 1102, the first flow rate value is calculated once there are enough sample flow rate values in the buffer for sufficient measurement at step 1103. The method returns after step 1103 to step 1100 to collect more data values for the buffer until the buffer is full. If the buffer is full at step 1102, the oldest values in the buffers are replaced with a values representative of a current flow rate at step 1107. These values in the buffer are averaged at step 1108 to produce a real-time flow rate. A microprocessor may direct the real-time flow rate to be displayed on a display device at step 1109.

In another embodiment, when a drop is detected at step 1101, a multiplier representing a volume per drop is increased in count and stored in the data buffer at step 1102. As the buffer fills with count values, cumulative volume may be tracked over a known period of time. Based on this information, the processor may further determine a real-time flow rate for fluid as each drop is detected at step 1101.

FIG. 12 shows an example data set of sensor readings for when milk is moving past the sensors used to determine flow rate and volume. FIG. 12A is a representation of signal data 1201 for when milk is passing in drops. If the signal is above a certain threshold 1203, then a drop 1202 is detected. A sample rate time $\Delta t$, is set in order to catch single drops as they fall. An alternative method is to read the sensor at smaller time intervals 1204, such that a peak detection method may detect the full signal profile of a single drop 1202 including its rise and fall. The time between drops $\Delta t_d$, may be used to calculate real-time flow rate. Alternatively, a preset time, such as the time to fill the averaging buffer, may be used to calculate real-time flow rate. FIG. 12B is a representation of signal data 1205 for when milk starts to pass in a continuous stream. In this case, the signal is above the threshold 1203 at every sampling time step $\Delta t$. The volume per drop is estimated from volume passed through the milk capture and collection system during pumping, and is based on the size and shape of the aperture or spout from which the milk falls from before passing the sensor. Multiple values for volume per drop, or a mapped multiplier, may be used depending on the time between drops $\Delta t_d$, and/or calculated flow rate, to more accurately predict exact volume as milk is expressed.

What is claimed is:

1. A breast pump sensor network, comprising: a plurality of emitters disposed within a bodily fluid capture system, which emit beams of electromagnetic radiation into the bodily fluid capture system, a plurality of detectors disposed within the bodily fluid capture system, wherein an emitter of the plurality of emitters is disposed adjacent to a corresponding detector of the plurality of detectors, so as to form a plurality of emitter and detector pairs, wherein bodily fluid is carried to a reservoir by a spout disposed in a flange and droplets of bodily fluid are output from the reservoir, the droplets being released from the reservoir at a known volumetric measurement, wherein the reservoir is disposed above the detector, below the flange, and above a valve within the bodily fluid capture system, wherein the reservoir allows the bodily fluid to pool in the reservoir and allows the droplets of the known volumetric measurement to fall from the reservoir, to be detected by during the fall, and fall into the valve which closes and opens based on vacuum pressure applied to the valve by vacuum suction, and a processor counting the detected droplets, and further comprising a lens configured to control reflections of the emitted electromagnetic radiation to direct reflections into the detector.

2. The breast pump sensor network of claim 1, wherein a beam of electromagnetic radiation is reflected by a bodily fluid into the detector.

3. The breast pump sensor network of claim 2, wherein the processor counts a number of drops of bodily fluid based on the detector detecting the reflected beam of electromagnetic radiation and determines a flow rate for the bodily fluid.

4. The breast pump sensor network of claim 1, further comprising:
    a body temperature sensor to detect a body temperature of a breast pump user.

5. The breast pump sensor network of claim 1, wherein the bodily fluid capture system includes a collection container to collect breast milk.

6. The breast pump sensor network of claim 1, further comprising:
    one or more sensors including at least one sensor disposed within a breast pump flange of the bodily fluid capture system.

7. The breast pump sensor network of claim 1, wherein the valve is a duckbill valve.

8. The breast pump sensor network of claim 1, wherein the plurality of emitter and detector pairs are disposed below the reservoir in the bodily fluid capture system.

9. The breast pump sensor network of claim 1, wherein the valve is closed when suction is applied within the bodily fluid capture system and wherein the valve is open when suction is released from the bodily fluid capture system and positive back pressure exists within the bodily fluid capture system.

10. The breast pump sensor network of claim 1, wherein the valve opens to release bodily fluids into a collection container attached to the bodily fluid capture system.

\* \* \* \* \*